United States Patent [19]

Chang et al.

[11] Patent Number: 5,229,304
[45] Date of Patent: Jul. 20, 1993

[54] METHOD FOR MANUFACTURING A SEMICONDUCTOR DEVICE, INCLUDING OPTICAL INSPECTION

[75] Inventors: Tao-Yuan Chang, Lincroft; Rubens da S. Miranda, Redbank; Harry W. K. Tom, Rumson, all of N.J.

[73] Assignee: AT&T Bell Laboratories, Murray Hill, N.J.

[21] Appl. No.: 878,101

[22] Filed: May 4, 1992

[51] Int. Cl.⁵ ............................................. H01L 21/326
[52] U.S. Cl. .......................................... 437/7; 437/174; 437/942
[58] Field of Search ................ 437/7, 8, 173, 174, 437/942, 943; 374/5; 356/432, 445

[56] References Cited

U.S. PATENT DOCUMENTS

| 4,636,088 | 1/1987 | Rosencwaig et al. | 356/445 |
| 4,917,462 | 4/1990 | Lewis et al. | 350/319 |
| 4,981,815 | 1/1991 | Kakoschke | 437/174 |
| 5,042,952 | 8/1991 | Opsal et al. | 356/432 |
| 5,126,569 | 6/1992 | Carlson | 356/432 |

OTHER PUBLICATIONS

R. S. Miranda, et al., "Use of time-resolved IR reflection and transmission as a probe of carrier dynamics in semiconductors", *Optics Lett.* 16, 1991, pp. 1859–1861.

*Primary Examiner*—Brian E. Hearn
*Assistant Examiner*—C. Chaudhari
*Attorney, Agent, or Firm*—Martin I. Finston; Eugen E. Pacher

[57] ABSTRACT

A method for manufacturing a semiconductor device which includes a step of evaluating the dopant profile, in at least the depth dimension, in a processed or partially processed wafer. The evaluation is performed nondestructively, by measuring a differential reflectivity spectrum of the doped portion of the wafer. The resulting spectrum can be related to the Fourier transform of the dopant profile in the depth dimension.

5 Claims, 3 Drawing Sheets

METHOD FOR MANUFACTURING A SEMICONDUCTOR DEVICE, INCLUDING OPTICAL INSPECTION

FIELD OF THE INVENTION

This invention relates to methods for evaluating the surface conditions of semiconductor bodies in order to determine the spatial distribution of dopants or electrical carriers. The invention is particularly suited for applications in the semiconductor industry, for example for monitoring manufacturing processes which lead to patterned distributions of dopants at and beneath the surfaces of semiconductor wafers.

ART BACKGROUND

Practitioners in the field of semiconductor device fabrication have long recognized the need to determine the sub-surface, compositional profiles of semiconductor wafers that have been processed, or partially processed. For example, dopant distributions produced by ion implantation followed by annealing are sensitive to process conditions such as implantation energy and the temperatures and durations which characterize the annealing cycle. It is important to measure the resulting distributions in order to establish appropriate process conditions. it is also important to measure the distributions from time to time during actual production of processed wafers, in order to assure that the manufacturing process is well controlled. For purposes of process initialization and control, it is important to measure the distributions in depth as well as in lateral dimensions.

As a further example, it is desirable during processing of, e.g., silicon wafers to diagnose the electronic properties at each processed layer within the wafer. For example, it may be desirable to distinguish layers at various depths which variously comprise crystalline, polycrystalline, and amorphous silicon.

Conventional techniques for the depth profiling of semiconductor substrates generally involve successive measurements, each performed after an incremental thickness has been removed from the wafer surface by ion sputtering or etching. The measurements performed by conventional, analytical instruments include, for example, capacitance measurements and direct analysis by secondary ion mass spectroscopy. Such techniques, however, are destructive and time-consuming. Especially for purposes of process monitoring and control, it is desirable to provide a depth profiling technique which non-destructive, and still more desirable to provide a technique which is also rapid. Such a technique is even more desirable if it can also be used for profiling in the lateral dimensions.

Non-destructive techniques have been reported for evaluating the compositions of semiconductor wafers at and very close to the wafer surface. Such techniques scan the surface of the sample with a modulated light beam (to be referred to as a "source beam"), and monitor the resulting time-dependent changes in reflectivity with a second light beam (to be referred to as a "probe beam"). The results of such measurments can be interpreted to yield information about compositional variations in depth as well as in the lateral dimensions. For example, U.S. Pat. No. 4,636,088, issued to A. Rosencwaig, et al. on Jan. 13, 1987, describes the use of the modulated beam to periodically heat the wafer surface. Because heating of the sample surface will change its reflectivity in a manner which is related to the local composition, compositional information can be deduced from the resulting modulations in the reflected probe beam. A second example is described in U.S. Pat. No. 5,042,952, issued to J. Opsal, et al. on Aug. 27, 1991. Described therein is a method in which the source beam is used to generate a periodic electron-hole plasma which interacts with features in the wafer as it diffuses. The resulting changes in the plasma density cause local alterations in the refractive index which, in turn, affect the reflectivity. The probe beam samples the plasma-induced, periodic reflectivity changes, yielding compositional information.

Although useful, the above-described optical methods are somewhat limited in spatial resolution in the depth dimension because they rely upon absorption of energy from the source beam. Therefore, those techniques are inherently limited to materials in which the source beam has a short penetration depth, which imposes a limit on the depth that can be probed. Moreover, the information which is collected by the probe beam represents an average in the depth dimension, down to the penetration depth. Therefore, it is not possible to achieve high spatial resolution in the depth dimension.

SUMMARY OF THE INVENTION

We have discovered that compositional variations at and to a significant depth below the surfaces of semiconductor bodies can be detected by scanning optical reflectometry. The reflectivity at each scanned wavelength will generally include a component which is attributable to a variation in the carrier density. The magnitude of such a component is related to the Fourier component of the carrier distribution in the depth dimension at a spatial frequency determined by the scanned wavelength. As a consequence, relatively high resolution in the depth dimension can be achieved by making an appropriate selection of scanned wavelengths. With the use of imaging optics, lateral resolution will generally be commensurate with the spot size of a probe beam focused on the surface of the semiconductor body. However, much finer resolution will be achievable through the use of a near-field optical probe. In contrast to the prior art, the inventive method does not require a substantial physical disturbance to be created in the semiconductor body. As a consequence, the method is readily practiced using a single optical beam.

The inventive method is particularly useful in the field of semiconductor device manufacturing, for purposes of process monitoring and control. Accordingly, in one embodiment, the invention involves a method for manufacturing a semiconductor device. The method includes the steps of: a) providing a multiplicity of semiconductor bodies, each body having a surface to be impressed with a distribution of dopant species, the distribution extending in the direction perpendicular to the surface and in the directions parallel to the surface; b) setting at least one process parameter; c) processing at least a first body according to the process parameter such that a dopant distribution is formed adjacent the surface of the body, the distribution having a profile, to be referred to as a "depth profile", extending into the body in said perpendicular direction; d) detecting the depth profile in at least the first body; e) comparing detected depth profile to a predetermined criterion; f) if the detected profile fails to satisfy the predetermined criterion, changing the process parameter to bring subsequently formed distributions into conformity with the predetermined criterion; g) after (f), processing at least a second body according to the process parameter; and h) performing, on at least the second body, at least one additional step toward completion of the semiconductor device. In a departure from techniques of the prior art, the "detecting" step comprises impinging on the surface of the first body electromagnetic radiation which comprises at least three principal wavelengths; and for each principal wavelength, measuring the reflectivity of the surface relative to that principal wavelength, such that a reflectivity spectrum is complied over the principal wavelengths. Moreover, the comparing step comprises comparing the reflectivity spectrum with the predetermined criterion. Significantly, in the inventive method, the depth profile is detected nondestructively.

DETAILED DESCRIPTION

Figure 1:
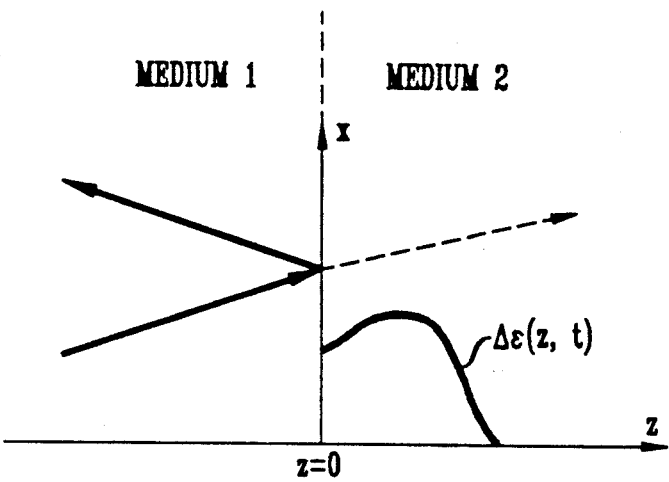
FIG. 1 is a schematic representation of the incident, transmitted, and reflected components of a probe beam being used to evaluate a sample, represented in the figure by medium 2, according to the invention.

We have solved Maxwell's equations for the reflection coefficients of $\hat{p}$-polarized and $\hat{s}$-polarized light from a semi-infinite slab (medium 2) which contains a perturbed distribution of carriers near the surface (i.e., within a few penetration depths of the interface with medium 1). We have assumed that, as predicted by the Drude model, a linear relation obtains between the dielectric function $\Delta\epsilon$ attributable to the perturbative carrier distribution, and the perturbative carrier density $n(z,t)$:

$$\Delta\epsilon(z,t) = (\delta\epsilon' + i\delta\epsilon'')n(z,t) \qquad \text{I}$$

In the following discussion, r represents the total reflection coefficient (at a given polarization and angle of incidence), $r^{(0)}$ represents the corresponding unperturbed reflection coefficient, and $\Delta R$ represents the differential reflectivity, defined as the difference between the absolute values, squared, of r and $r^{(0)}$. We have derived a relationship which shows that $\Delta R$ is a function of the Fourier transform of $n(z,t)$ at spatial frequency $2k_{2z}$, where $k_{2z}$ is the z-component of the wavevector of the incident radiation in medium 2. (The z direction is the direction normal to the interface between medium 1 and medium 2.) That is, to a good approximation, $\Delta R$ may be expressed by $$\Delta R = fn\left\{\int_0^L (\delta\epsilon'\sin 2k_{2z}z + i\delta\epsilon''\cos 2k_{2z}z)n(z,t)dz\right\} \qquad \text{II}$$

where the notation fn{ } indicates that the left-hand side of the equation is a function of the expression enclosed in braces on the right-hand side. The details of the derivation of Equation II are published in R. S. Miranda, et al., "Use of time-resolved IR reflection and transmission as a probe of carrier dynamics in semiconductors," *Optics Letters* 16 (1991) 1859–1861, incorporated herein by reference. The functional dependence fn can be determined from the detailed derivation, or, alternatively, it can be empirically determined from experimental measurements on a sample of known properties.

According to Equation II, provided the relation between the dielectric constant and the carrier density is known, the carrier density can be determined as a function of depth and time by probing with a range of wavelengths wide enough to resolve spatial frequencies of interest. Equation II embodies an assumption that such relation is linear. In fact, the analysis which led to Equation II is readily generalized to an arbitrary relation between $\delta\epsilon$ and n. In such a case, for quantitativley solving Equation II for n, it will be useful to provide a table, based on independent calculations or measurements, which explicitly defines such relation over an appropriate range of values of $\delta\epsilon$ and n.

The carrier density in a sample can also be determined as a function of lateral position (i.e., positions parallel to the interface between medium 1 and medium 2) by scanning the sample with a focused probe beam. The lateral resolution achievable by such means is limited primarily by the size of the spot that can be focused on the sample. Still finer lateral resolution can be achieved by near-field scanning optical microscopy (NSOM), using a suitable near-field probe such as a tapered metal capillary or (in a compatible spectral range) a tapered and metallized glass pipette. An NSOM instrument using a glass pipette probe is described in U.S. Pat. No. 4,917,462, issued to A. Lewis et al. on Apr. 17, 1990, and is incorporated herein by reference.

Often, the process steps which are involved in manufacturing semiconductor devices on a semiconductor wafer include the formation of spatially dependent dopant distributions at and below the surface of the wafer. Such distributions can be measured by scanning in the lateral directions with a suitable probe beam, and, at least at selected positions within the scan pattern, by measuring the differential reflectivity as the probe wavelength is varied over a suitable range. At each wavelength, Equation II may, in effect, be solved to obtain the Fourier component of $n(z)$ corresponding to that wavelength. That is, at each optical wavelength $\lambda$, the spatial frequency which is probed is equal to the wavenumber $k_{2z}$, which is given by the expression:

$$k_{2z} = \frac{2\pi}{\lambda}\sqrt{\epsilon_2 - \epsilon_1\sin^2\theta} \qquad \text{III}$$

In the preceding equation, $\epsilon_1$ and $\epsilon_2$ represent the respective dielectric constants in medium 1 and medium 2 (see FIG. 1), and $\theta$ represents the angle of incidence of the probe beam on the sample. (We have typically used values of $\theta$ in the range 35°–75°.)

For such diagnosis of semiconductor wafers, steady-state carrier distributions, and not time-dependent distributions, will generally be measured. Thus, a pulsed laser probe source will generally not be required. Instead, an appropriate source of probe light will be, for example, a cw laser which is tunable over a wavelength range which provides the desired spatial resolution in the depth direction (i.e., the z-direction), and which can provide a rapid sweep over such wavelength range. An alternate source of probe light is a wideband source combined with a frequency-selective optical system such as an interferometer. For probing in the infrared wavelength region, commercially available FTIR instruments incorporate useful light sources and detectors. Still another alternate source of probe radiation is an array of infrared laser diodes which emit at selected wavelengths.

If, in fact, a pulsed laser probe is used, additional useful information can be obtained. That is, a pulsed source can, additionally, yield dynamical information about carrier densities in the sample. Such dynamical information includes, for example, carrier lifetimes. Thus, for example, the quality of an oxide layer can be evaluated without the need for electrical contacts by measuring the surface recombination rate at the oxide interface. Another application for a pulsed laser source is for testing an operating semiconductor device. That is, the carrier distribution may change as the operating conditions of such a device are changed. Changes in the carrier distribution can be observed according to the inventive method if, for example, the timing of the probe pulses is varied relative to a modulation cycle in the driving circuit of the device. The use of the inventive method to derive dynamical information is described in R. S. Miranda, et al., *Optics Letters* 16 (1991) 1859-1861, referred to above.

For some applications, it will be unnecessary to reconstruct the dopant distribution n(z) from the differential reflectivity. For example, it might be desirable to use differential reflectivity measurements to verify that dopant distributions lie within predetermined manufacturing tolerances. A simplified verification procedure is readily practiced if there is available a wafer which has already been patterned with the desired dopant distributions, and which can be used as a standard. If that is the case, the differential reflectivity measurements from the sample wafers can be compared directly with the corresponding measurments from the standard wafer. Appropriate limits on the deviations between the sample and standard measurements can be selected, such that if the deviations fall within the selected limits, conformity to the required manufacturing tolerances is assured.

It is advantageous to probe, e.g., a gallium arsenide sample with infrared, rather than with visible, light, because gallium arsenide is transparent to infrared wavelengths (in at least a certain range). As a result, the differential reflectivity that is measured will depend on the spatial profile of the carriers throughout the depth of the sample. Moreover, for wavelengths long enough, the differential reflectivity will be attributable primarily to free carriers, and will be free of the detailed spectroscopic structure that typically appears in visible-wavelength spectra.

However, the spatial resolution achievable in the z-direction is dependent upon the probe wavelengths. More specifically, the spatial frequency $k_\lambda$ which is sampled at a given wavelength $\lambda$ is given approximately by $$k_\lambda \approx \frac{40}{\lambda}.$$

Thus, it may be advantageous to probe with visible wavelengths in order to achieve the greatest possible resolution, even though optical absorption in the visible range may complicate the interpretation of the measurements. Such complication may be tolerable if, for example, it is sufficient to compare the differential reflectivity data directly with those from a standard wafer. For example, it is advantageous to probe at least some silicon structures with visible light, in order to achieve sufficient resolution to examine features lying at depths as shallow as about 500 Å, and having characteristic dimensions (in the z-direction) as small as about 50 Å. Because at least some visible wavelengths will penetrate as deeply as about 1000 Å in silicon, features having those characteristics will be detectable.

Figure 4:
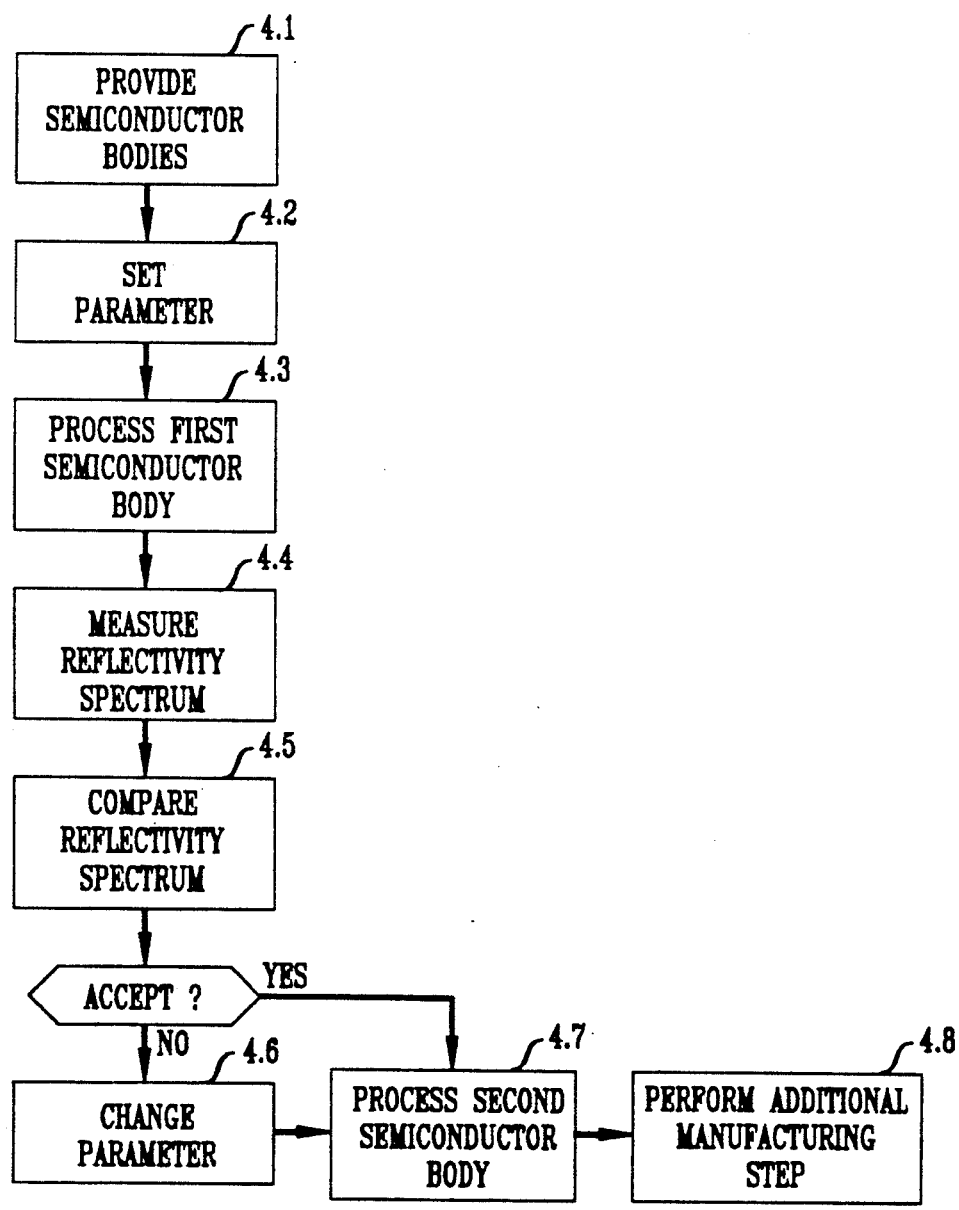
FIG. 4 is a flowchart of a manufacturing process, according to the invention in one embodiment.

The invention, in one embodiment illustrated schematically in FIG. 4, involves a method for manufacturing a plurality of integrated circuits. The method includes the steps of providing a plurality of semiconductor wafers, each having a principal surface (Step 4.1 of the figure), and processing the wafers such that a patterned dopant distribution is formed at and below the principal surface of each (Step 4.3 and subsequent steps). The processing is carried out, for example, by ion implantation of the dopant species, followed by annealing. In order to assure that an acceptable proportion of the manufactured circuits will function properly, it is often important for both the depth profile and the lateral profile of the dopant distribution to satisfy specified manufacturing tolerances. To satisfy the specified tolerances, it may be necessary to adjust the initial setting of process parameters (Step 4.2) based on diagnostic information.

For example, a typical post-anneal implant depth profile for GaAs MESFETs is 2000 Å deep and 2000 Å wide. Numerical simulations have indicated that by scanning infrared wavelengths of 2 μm-20 μm, the practitioner will, in at least some cases, be able to distinguish 2000 Å deep profiles from profiles which are 2500 Å deep. Using infrared wavelengths the practitioner will be able to distinguish features even at depths substantially greater than 1 μm within GaAs substrate. Using commercially available laser sources and standard, imaging optics, the practitioner will be able to achieve a lateral resolution of 20 μ m or better. Using an NSOM probe, the practitioner will be able to achieve a lateral resolution of about one probe wavelength, or better.

If the relevant process step results in a dopant distribution which falls outside of the specified criteria, it is often desirable to adjust process parameters (Step 4.6) such as the implant energy, annealing temperature, and annealing time, in order to bring the dopant distribution in subsequently processed wafers (Step 4.7 and 4.8) into conformity with the manufacturing tolerances. Process quality may be monitored by examining selected, processed wafers. Such monitoring is readily performed according to the invention by measuring the differential reflectivity of each such selected wafer while the probe wavelength is being scanned (Step 4.4). A selected location or group of locations on the wafer may be examined, or, alternatively, the probe beam may scan many points on the surface of the wafer (in, e.g., a raster pattern) in order to provide information on the lateral profile as well as the depth profile of the dopant distribution.

In a currently preferred embodiment of the invention, each selected wafer is evaluated by comparing its reflectivity measurements with corresponding measurements made on a previously prepared standard wafer (Step 4.5). If the measurements differ unacceptably (according to predetermined criteria), the process parameters are adjusted accordingly (Step 4.6).

Significantly, the inventive method can be used to evaluate the condition of a semiconductor substrate during real-time processing. For example, during post-implant annealing, the as-deposited dopant profile changes as the dopant species diffuse within the substrate. It is often desirable to stop the annealing process when the diffusion has proceeded to a precise depth into the substrate. Unlike conventional analytical methods, the inventive method can be used to monitor the dopant profile during annealing. Because the sample is probed by a beam of electromagnetic radiation, it is not necessary to handle the sample while it is being evaluated. Consequently, the dopant profile can be monitored without removing the sample from the annealing chamber, and without interrupting the annealing process.

A simplified probe for evaluating a processed semiconductor substrate may consist of as few as three single-wavelength radiation sources, such as laser diodes, emitting at three distinct, predetermined wavelengths. The wavelengths are chosen to correspond to identifying features of the reflectivity spectrum which corresponds to the desired dopant profile. Thus, the chosen wavelengths will typically correspond to the main Fourier peaks of the desired profile. The ratios of the respective reflectivities probed by the three sources provide an indication of when the desired profile has been (at least approximately) achieved.

EXAMPLE

Figure 2:
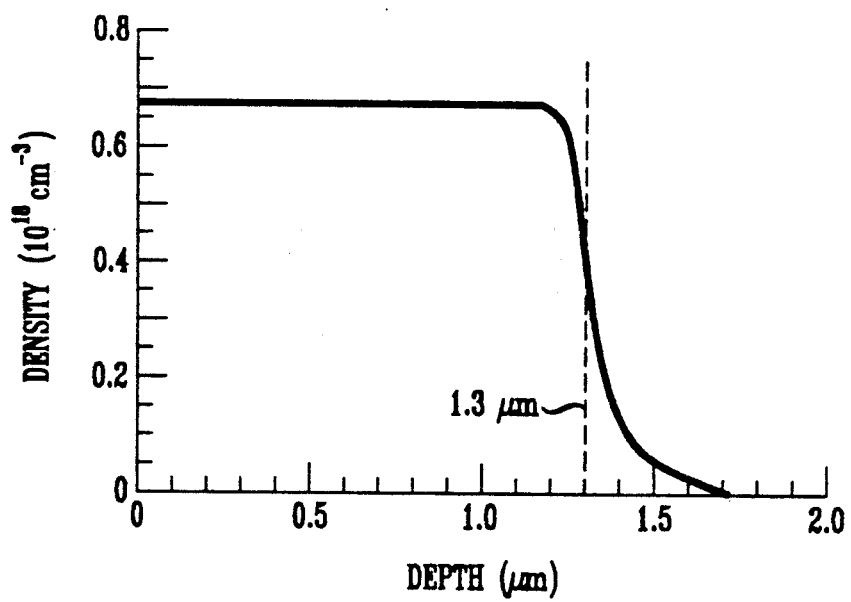
FIG. 2 is a graph of the electron profile in an illustrative, doped sample suitable for evaluation according to the inventive method.
Figure 3:
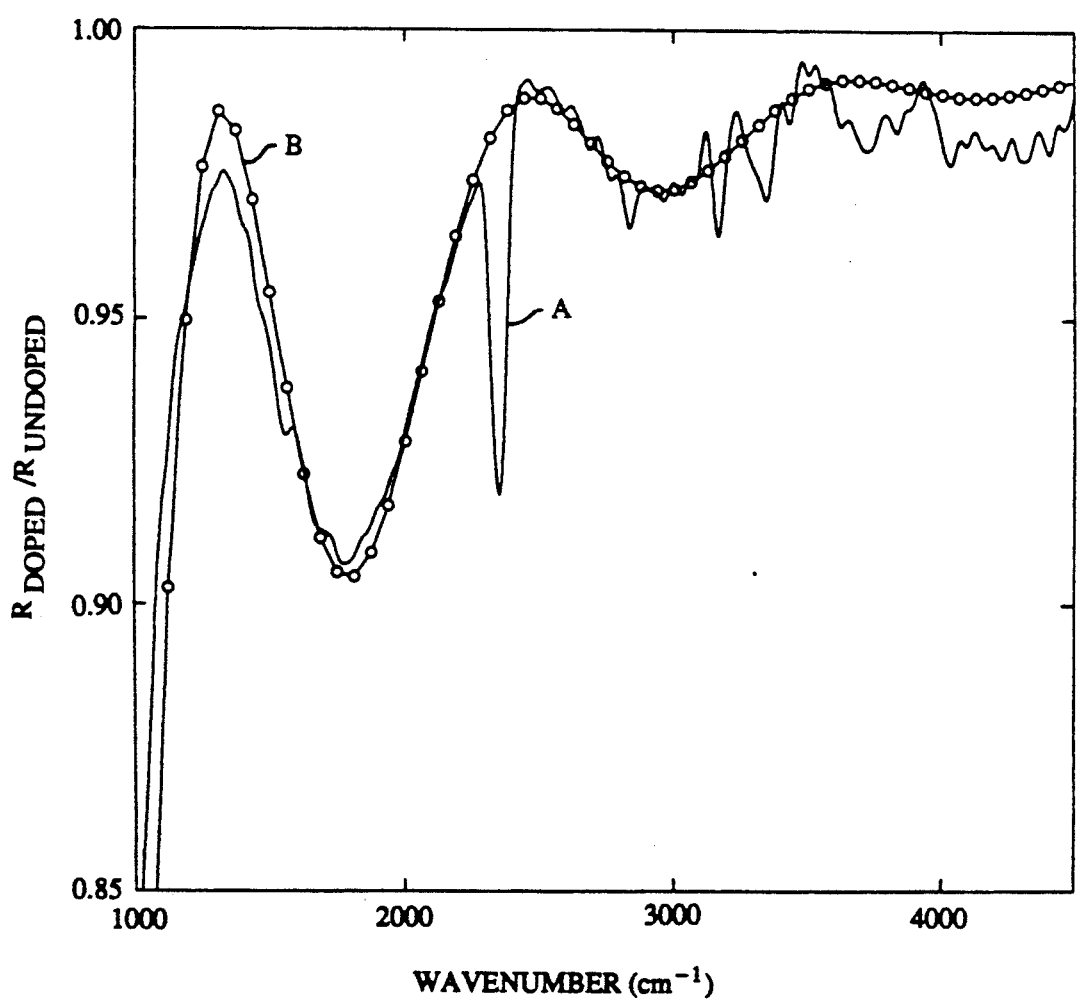
FIG. 3 is a reflectivity spectrum of the sample of FIG. 2, displayed together with a theoretical curve which represents the Fourier transform of the electron distribution of FIG. 2.

A sample of GaAs implanted with silicon was provided. The variation of electron density as a function of depth within the sample is shown in FIG. 2. We measured a continuous reflectivity spectrum from the sample, using a commercially available FTIR spectrometer. Curve A of FIG. 3 represents the spectrum as the ratio of reflectivity from the doped sample to reflectivity from an undoped, reference sample. The pronounced negative peak visible in the figure at a wavenumber of about 2300 $cm^{-1}$ is caused by optical absorption by an atmospheric gas, probably carbon monoxide. The structure visible in the spectrum in the range 3000–4500 $cm^{-1}$ is at least partially attributable to absorption by water vapor. We performed a theoretical fit of the reflectivity spectrum to the Fourier transform of the electron profile of FIG. 2. The theoretical curve is labeled "B" in FIG. 3. From the theoretical fit, we obtained an accurate value (i.e., 1.3 $\mu m$) for the width of the electron distribution. However, our estimate of the absolute value of the electron density agreed with the known value only to within about a factor of 2.5, due to uncertainties in calibration.

We claim:
1. A method for manufacturing a semiconductor device, which comprises the steps of:
   a) providing a multiplicity of semiconductor bodies, each body having a surface to be impressed with a distribution of dopant species, the distribution extending in the direction perpendicular to the surface and in the directions parallel to the surface;
   b) setting at least one process parameter;
   c) processing at least a first body according to the process parameter such that a dopant distribution is formed adjacent the surface of the body, the distribution having a profile, to be referred to as a "depth profile", extending into the body in said perpendicular direction;
   d) detecting the depth profile in at least the first body;
   e) comparing the detected depth profile to a predetermined criterion;
   f) if the detected profile fails to satisfy the predetermined criterion, changing the process parameter to bring subsequently formed distributions into conformity with the predetermined criterion;
   g) after (f), processing at least a second body according to the process parameter; and
   h) performing, on at least the second body, at least one additional step toward completion of the semiconductor device,
   Characterized That
   i) the detecting step comprises impinging on the surface of the first body electromagnetic radiation which comprises at least three principal wavelengths; and for each principal wavelength, measuring the reflectivity of the surface relative to that principal wavelength, such that a reflectivity spectrum is compiled over the principal wavelengths; and
   j) the comparing step comprises comparing the reflectivity spectrum with the predetermined criterion.

2. The method of claim 1, wherein the detecting step comprises impinging on the surface of the first body a probe beam of electromagnetic radiation narrowly distributed about a principal wavelength, and varying the principal wavelength over a predetermined range, such that a continuous reflectivity spectrum can be compiled over the predetermined range.

3. The method of claim 1, wherein the detecting step comprises impinging on the surface of the first body at least three probe beams of electromagnetic radiation, each probe beam narrowly distributed about a distinct, fixed, principal wavelength, such that a discrete reflectivity spectrum can be compiled over the principal wavelengths.

4. The method of claim 1, wherein the detecting step comprises impinging on the surface of the first body a probe beam of electromagnetic radiation distributed continuously over a spectral range, such that at least a portion of the radiation is reflected from the surface; and the detecting step further comprises collecting and spectrally discriminating a portion of the reflected radiation such that a reflectivity spectrum can be compiled over at least a portion of the spectral range.

5. A method for manufacturing a semiconductor device, which comprises the steps of:
   a) providing at least first and second semiconductor bodies, each body having a surface impressed with a distribution of dopant species, the distribution extending in the direction perpendicular to the surface and in the directions parallel to the surface;
   b) setting at least one annealing temperature and annealing time;
   c) annealing the first and second bodies according to the annealing temperature and annealing time, such that a dopant diffusion profile is formed adjacent the surfaces of the bodies and extending into the bodies in the perpendicular direction;
   d) during (c), detecting the depth profile in at least the first body;
   e) comparing the detected depth profile to a predetermined criterion;

f) adjusting the annealing time and/or the annealing temperature in accordance with the result of step (e); and g) performing, on at least the second body, at least one additional step toward completion of the semiconductor device, Characterized That i) the detecting step comprises impinging on the surface of the first body electromagnetic radiation which comprises at least three principal wavelengths; and for each principal wavelength, measuring the reflectivity of the surface relative to that principal wavelength, such that a reflectivity spectrum is compiled over the principal wavelengths; and j) the comparing step comprises comparing the reflectivity spectrum with the predetermined criterion.

* * * * *